United States Patent [19]

Keller

[11] Plant 5,238

[45] May 29, 1984

[54] DISTINCT VARIETY OF STREPTOCARPUS NAMED ORCHIS

[75] Inventor: Emil Keller, Hedingen, Switzerland

[73] Assignee: Oglevee Associates, Inc., Connellsville, Pa.

[21] Appl. No.: 452,819

[22] Filed: Dec. 28, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

The new cultivar is generally characterized by its two-tone rose pink and purple coloration and its distinct veining. It is also characterized by flower stalks which are open and of irregular length.

1 Drawing Figure

BACKGROUND OF THE NEW PLANT

The present invention comprises a new and distinct cultivar of *Streptocarpus* × *hybridus* known by the varietal name of Orchis. The new cultivar was developed in a breeding program and is a cross of the varieties Fiona (pollen parent) and Karen (seed parent). The new cultivar is distinguished from its parentage by its brighter color, yellow throat and early blooming. It is similar to its parentage in respect of its pink color, design of flower and strong peduncles.

The new cultivar is generally characterized by its two-tone rose pink and purple coloration and its distinct veining. It is also characterized by flower stalks which are open and of irregular length.

The new cultivar was discovered in 1978 in Hedingen, Switzerland; was first asexually reproduced by cuttings in Hedingen, Switzerland; and has been repeatedly asexually reproduced by cuttings at Oglevee Floral Company in Connellsville, Pa. It has been found to retain its distinctive characteristics through successive propagations.

The new cultivar, when grown in a greenhouse in Connellsville, Pa. has a response time of nine weeks. This response time is measured from a plantlet which is a well rooted young plant in a five centimeter pot to a flowering plant in a fifteen centimeter pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out by the Oglevee Floral Company in Connellsville, Pa. The plant history was taken on nine week plants blossomed under natural light in a greenhouse and color readings were also taken using natural sunlight. Color references are primarily to the R.H.S. color chart of The Royal Horticultural Society of London. Some color reference is to Exotica III and such reference is duly noted.

Botanical classification: Gesneriaceae (family); *Streptocarpus* × *hybridus* (genus × species).

Flower:

*Fully expanded.*—4.5 to 5.5 centimeters.

*Borne.*—In clusters of 4 to 10 flowers per flower stalk. Flower stalks are irregular in size and direction giving overall irregular appearance.

*Stems.*—Single, long, round and pubescent.

*Form.*—Funnel formed in an umbel.

*Permanence.*—Long lasting 21 to 25 days.

Color:

*Tonality from a distance.*—Two-tone rose pink to purple with purple veining. Throat is streaked with mimosa yellow (Exotica III).

*Front of petals.*—Background color is Fan 2 Red Purple Group 66-D, toning is Fan 2 Red Purple Group 66-B. Veining is Fan 2 Red Purple Group 74-A.

*Throat.*—Fan 1 Yellow Group 7-D.

*Reverse of petals.*—Fan 2 Purple Group 75-C.

*Discoloration.*—Insignificant.

Petals:

*Texture.*—Velvet.

*Appearance.*—Individually lobed, informal lobing with cuneate margins.

*Arrangement.*—Regularly united into elliptical form.

*Persistence.*—21 to 25 days and remains on plant in dry form until picked.

*Fragrance.*—None.

Reproductive organs:

*Anthers.*—Four per flower, some have imperfectly formed stamens, middle two are interconnected.

*Filament.*—The perfectly formed ones are 0.6 centimeter and attach to petals about 1.5 centimers up from base; the imperfectly formed ones start 1.5 centimeters up from base and extend 1 to 3 millimeters.

*Pollen.*—Generally nonfertile.

*Style.*—0.4 centimeter from tip of ovary to flattened stigma which is purplish cast.

*Ovaries.*—Include purple streaks and are long and narrow being 2 centimeters long and 2 millimeters in diameter.

Plant:

*Form.*—Leaves rosette from a crown at the soil line.

*Growth.*—A spreading, irregular habit.

*Height from soil line.*—15 to 25 centimeters.

*Spread.*—35 to 45 centimeters.

Foliage:

*Top side.*—Fan3 Green Group 137-C.

*Under side.*—Fan 4 Greyed Green Group 193-A.

*Size.*—15 to 30 centimeters in length and 7.5 to 10 centimeters wide at widest point.

*Quantity.*—5 to 7 leaves.

*Shape.*—Elliptical.

*Ribs and veins.*—Pinnate.

*Rib and vein color.*—Fan 3 Green Group 138-D.

*Margin.*—Cuneate and slightly lobed.

*Leaf tips.*—Obtuse.

*Leaf base.*—Attenuate.

I claim:

1. A new and distinct variety of Streptocarpus substantially as herein shown and described.

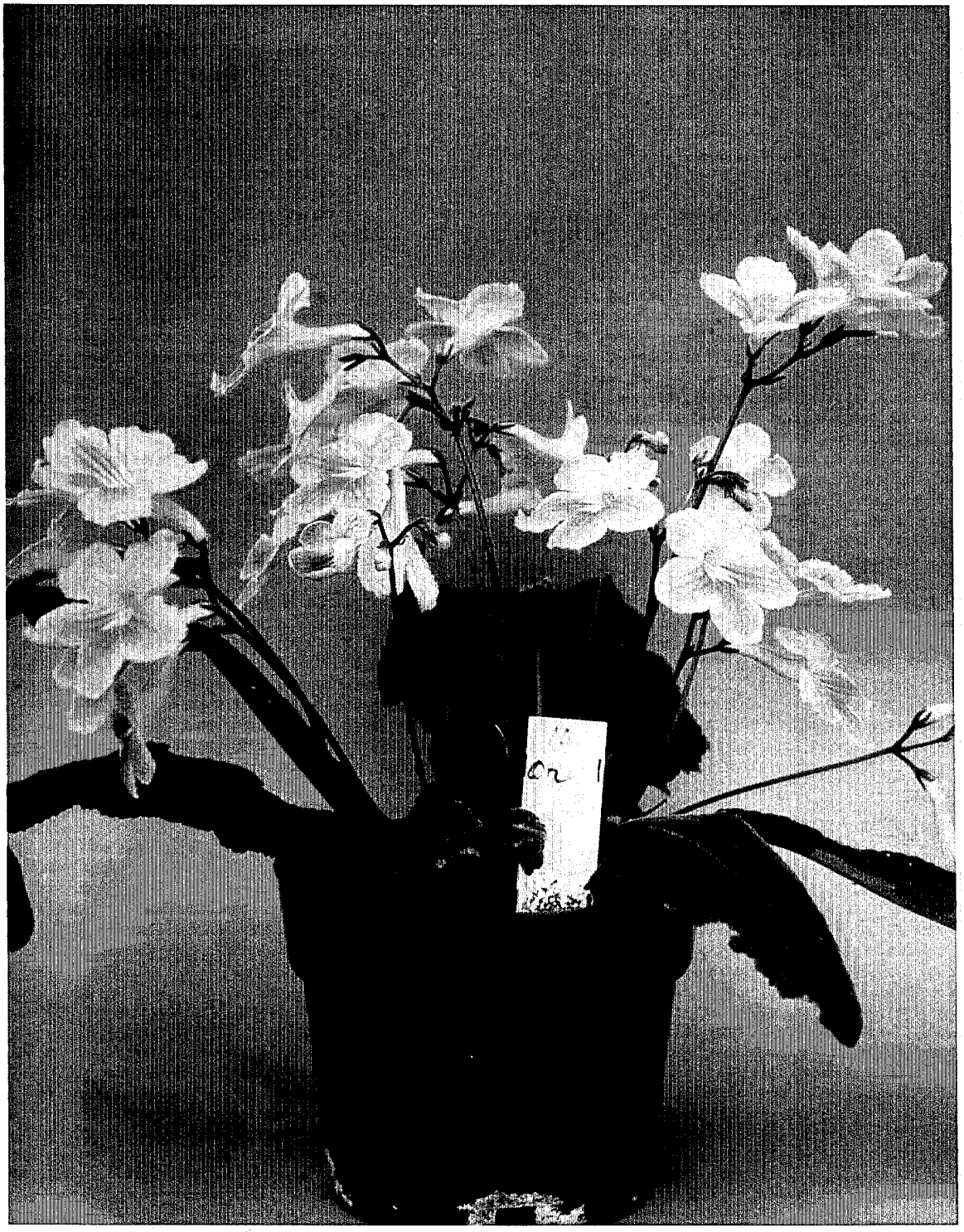

* * * * *